United States Patent [19]

Shewen et al.

[11] Patent Number: 5,378,615
[45] Date of Patent: Jan. 3, 1995

[54] PROCESS FOR THE PRODUCTION OF VACCINE FOR PREVENTION OF PASTEURELLA HAEMOLYTICA PNEUMONIA IN BOVINE

[75] Inventors: Patricia E. Shewen, Guelph; Bruce N. Wilkie, Puslinch, both of Canada

[73] Assignee: The University of Guelph, Canada

[21] Appl. No.: 958,796

[22] Filed: Oct. 9, 1992

Related U.S. Application Data

[63] Continuation of Ser. No. 462,929, Jan. 12, 1990, Pat. No. 5,165,924, which is a continuation of Ser. No. 821,197, Jan. 22, 1986, abandoned.

[51] Int. Cl.⁶ ............... A61K 39/00; A61K 39/02; C12P 21/00; C12N 1/20
[52] U.S. Cl. .................. 435/71.3; 435/252.1; 424/255.1
[58] Field of Search ............. 435/71.3, 252.1; 424/88, 92

[56] References Cited

U.S. PATENT DOCUMENTS

| | | | |
|---|---|---|---|
| 4,285,931 | 8/1981 | Limjuco et al. | 424/92 |
| 4k346,074 | 8/1982 | Gilmour et al. | 424/92 |
| 4,957,739 | 9/1990 | Berget et al. | 424/92 |
| 5,028,423 | 7/1991 | Prickett | 424/85.8 |

OTHER PUBLICATIONS

Baluyut, et al., *Am. J. Vet. Res.*, vol. 42, p. 1920–1926 1981.
Lo et al., *Infection and Immunity*, 1985, vol. 50, pp. 667–671.
Wilkie, "Principles of Biological Control of Shipping Fever", *The Bovine Proceedings*, 13:113–114 (Apr. 1981).
Wilkie, "Humoral and Cell–Mediated Resistance Mechanisms of Cattle", *Bovine Respiratory Disease*, pp. 102–142 (1984).
Shewen, "Cytocidal Toxins of Gram–Negative Rods", *Virulence Mechanisms of Bacterial Pathogens*, pp. 231–233 (1988).
Wilkie et al, "Bovine Pasteurellosis; A Biotechnological Approach to Control", *The Bovine Proceedings*, 21:52–55 (Apr. 1988).
Shewen, "*Pasteurella Haemolytica*: Virulence Mechanisms and Protective Immunity in Cattle", *Proc. 9th Acvim Forum*, pp. 531–533 (May 1991).
Shewen et al, "Prevention of Bovine Pneumonic Pasteurellosis", *Highlights*, 8:4–6 (Sep. 1985).
Shewen, "*Pasteurella*", In: *Pathogens of Bacterial Infections in Animals*, pp. 150–151 (1986).
Shewen et al, "*Pasteurella Haemolytica* Cytoxin Neutralizing Activity in Sera from Ontario Beef Cattle", *Can. J. Comp. Med.*, 497–498 (1983).
Otulakowski et al, "Proteolysis of Sialoglycoprotein by *Pasteurella Haemolytica* Cytotoxic Culture Supernatant", *Infection and Immunity*, 42(1):64–70 (1983).
Wilkie et al, "Defining the Role that *Pasteurella Haemolytica* Plays in Shipping Fever", *Vet. Medicine*, pp. 1053–1058 (Oct. 1988).
Jim et al, "Protecting Feedlot Claves from Pneumonic Pasteurellosis" *Vet. Medicine*, pp. 1084–1087 (Oct. 1988).
Majury et al, "The Effect of *Pasturella Haemolytica* A1 Leukotoxic Culture Supernate on the *in vitro* Proliferative Response of Bovine Lymphocytes", 29:41–56 (1991).

(List continued on next page.)

*Primary Examiner*—Irene Marx
*Attorney, Agent, or Firm*—Sughrue, Mion, Zinn, Macpeak & Seas

[57] ABSTRACT

A serum-free vaccine effective against pneumonic pasteurellosis in cattle comprising a non-toxic leukotoxin specific for ruminant leukocytes is disclosed. The leukotoxin is prepared in a serum-free medium from a culture of *Pasteurella haemolytica*. The produced leukotoxin is harvested from the culture medium upon detecting a certain stage during the logarithmic phase of the cell growth to obtain the optimum concentration of produced cytotoxin in the serum-free medium. Cattle may be treated with the vaccine to develop anti-leukotoxic immunity to pneumonic pasterellosis.

7 Claims, 2 Drawing Sheets

OTHER PUBLICATIONS

Lo et al, "Molecular Studies of Ssa1, a Serotype-Specific Antigen of *Pasteurella Haemolytica* A1", *Infection and Immunity*, 59(10):3398–3406 (Oct. 1991).

Abdullah et al, "A Neutral Glycoprotease of *Pasteurella Haemolytica* A1 Specifically Cleaves O-Sialoglycoproteins", *Infection and Immunity*, 60(1):56–62 (Jan. 1992).

Shewen et al, "Anitbody Titers to *Pasteurella Haemolytica* A1 in Ontario beef Cattle", *Can. J. Comp. Med.*, 46:354–356 (Oct. 1982).

Shewen et al, "Immunity ot the *Pasteurella Haemolytica* Cytotoxin", *63rd Conf. Red. Work. An. Dis.*, p. 26 (Nov. 1982).

Gonzalez-Rayos et al, "Cloning of a Serotype-Specific Antigen from *Pasteurella Haemolytica* A1", *Infection and Immunity*, 53(3):505–510 (Sep. 1986).

Shewen et al, "Immunity to *Pasteurella Haemolytica* Serotype 1", *North American Symposium on Bovine Respiratory Disease*, pp. 480–481 (Sep. 1983).

Lo et al, "A Simple Immunological Detection Method for the Direct Screening of Genes from Clone Banks", *Biochem. Cell Biol.*, 64:73–76 (1986).

Shewen et al, "Vaccincation of Calves with Leukotoxic Culture Supernatant from *Pasteurella Haemolytica*", *Can. J. Vet. Res.*, 52:30–36 (1988).

Conlon et al, "Efficacy of Recombinant Leukotoxin in Protection Against Pneumonic Challenge with Live *Pasteurella Haemolytica* A1", *Infection and Immunity*, 59(2):587–591 (Feb. 1991).

Shewen et al, "Cytotoxin of *Pasteurella Haemolytica* Acting on Bovine Leukocytes", *Infection and Immunity*, 35(1):91–94 (Jan. 1982).

Himmel et al, "Purification and Partial Characterization of a Macrophage Cytotoxin from *Pastuerella Haemolytica*", *Am. J. Vet. Res.*, 43(5):764–767 (May 1982).

Gentry et al, "Serum Naturalization of Cytotoxin from *Pasteurella Haemolytica*, Serotype 1 and Resistance to Experimental Bovine Pneumonic Pasteurellosis", *Vet. Immuno. Immunopath.*, 9:239–250 (1985).

Cho et al, "Anticytotoxin Activity of Bovine Sera and Body Fluids Against *Pasteurella Haemolytica* A1 Cytotoxin", *Can. J. Comp. Med.*, 48:151–155 (1984).

Lo et al, "Nucleotide Sequence of the Leukotoxin Genes of *Pasteurella Haemolytica* A1", *Infection and Immunity*, 55(9):1987–1996 (Sep. 1987).

Mosier et al, "Chromatographic Separation and Characterization of *Pasteurella Haemolytica* Cytotoxin", *Am. J. Vet. Res.*, 47(10):2233–2241 (Oct. 1986).

Strathdee et al, "Extensive Homology between the Leukotoxin of *Pasteurella Haemolytica* A1 and the Alpha-Hemolysin of *Escherichia coli*", *Infection and Immunity*, 55(12):3233–3236 (Dec. 1987).

Highlander et al, "Secretion and Expression of the *Pasteurella haemolytica* Leukotoxin", *J. of Bacteriology*, 172(5):2343–2350 (May 1990).

Lo, "Molecular Characterization of Cytotoxins Produced by *Haemophilus, Actinobacillus, Pasteurella*", *Can. J. Vet. Res.*, 54:s33–s35 (1990).

Strathdee et al, "Cloning, Nucleotide Sequence, and Characterization of Genes Encoding the Secretion Function of the *Pasteurella Haemolytica* Leukotoxin Determinant", *J. Bacteriol.*, 171(2):916–928 (1989).

Chang et al, *Am. J. Vet. Res.*, 47:67–74 (1986).

Shewen et al, *Am. J. Vet. Res.*, 44:715–719 (1983).

Simpson et al, *Infect. Immun.*, 56:1162–1166 (1988).

Scanlan et al, *Am. J. Vet. Res.*, 43:1239–1333. (1982).

Baluyet et al, *Am. J. Vet. Res.*, 42:1920–1926 (1981).

Krieg et al, *Bergey's Manual of Systematic Bacteriology*, Williams and Wilkens, p. 556 (1984).

Shewen et al, *Vet. Med.*, 83:1078–1083 (1988).

Chang et al, *Infect. Imm.*, 55:2348–2354 (1987).

Sutherland et al, *Vet. Micro.* 11:331–336 (1986).

Shewen et al, North American Symposium on Bovine Respiratory Disease, Amarillo, Tex., Dec, 11983 (Abstract).

Davis et al, *Microbiology*, 3rd edition, pp. 64–65 (1980).

Shewen et al, *Am. J. Vet. Med.*, 46:1212–1214 (1985).

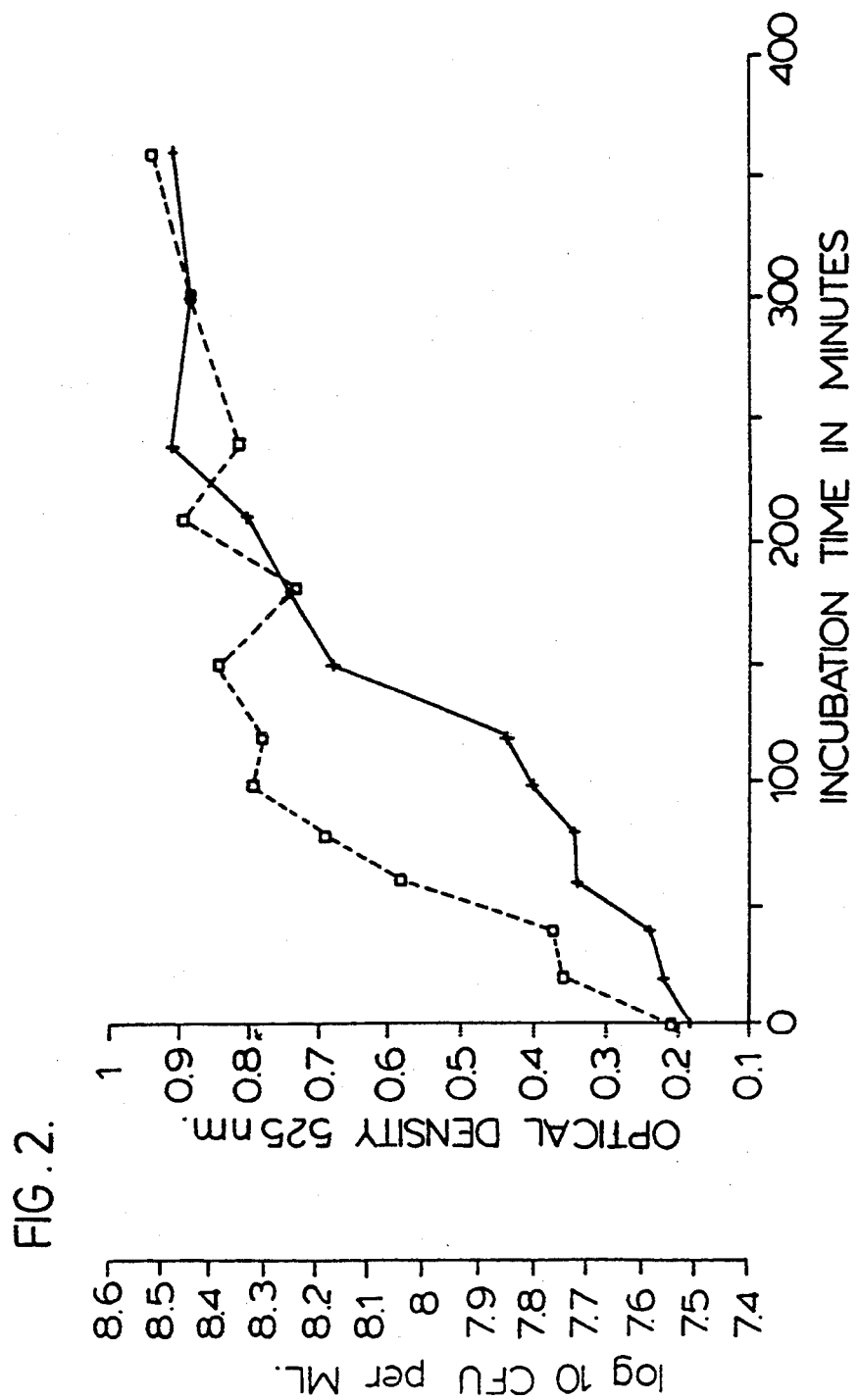

PROCESS FOR THE PRODUCTION OF VACCINE FOR PREVENTION OF PASTEURELLA HAEMOLYTICA PNEUMONIA IN BOVINE

This is a continuation of U.S. application Ser. No. 07/462,929, filed Jan. 12, 1990, now U.S. Pat. No. 5,165,924, which is a continuation of U.S. application Ser. No. 06/821,197, filed Jan. 22, 1986, now abandoned.

FIELD OF THE INVENTION

This invention relates to vaccines and processes for making same which are effective against a type of pneumonia in animals.

BACKGROUND OF THE INVENTION

In the raising of animals for commercial purposes, various strains of pneumonia causing organisms can be a significant cause of animal death. More particularly in the raising of cattle, "Shipping Fever" pneumonia is the major cause of sickness and mortality in feedlot cattle in North America. Although several respiratory viruses and bacteria have been implicated in the pathogenesis of the syndrome, the principal well known organism isolated is *Pasteurella haemolytica* serotype A1. The disease can be reproduced experimentally by intratracheal inoculation of the microorganism. Bacterins incorporating *P. haemolytica* have been in use for more than sixty years in preventing this disease without significant impact on disease control. Evidence from field studies and experimental trials suggests an adverse effect of vaccination using the bacterins. Animals vaccinated with inactivated whole cell bacterins frequently show a higher incidence of pneumonia and more severe lesions at post mortem than do unvaccinated animals. This occurs despite the induction of serum antibody to *P. haemolytica* cell surface antigens, measured by bacterial agglutination or passive hemaglutination techniques. This has resulted in considerable confusion with respect to how this type of pneumonia can be prevented. Paradoxically, the occurrence of an analogous response as a result of natural or experimental infection with live bacteria has resulted in developing a degree of immunity to pneumonia in so infected animals.

It has been determined that culture supernatant of *Pasteurella haemolytica* is cytotoxic to bovine but not porcine cells, as reported in "Cytotoxin of *Pasteurella haemolytica* Acting on Bovine Leukocytes", P. E. Shewen and B. N. Wilkie, Infection and Immunity, January 1982, Vol. 32 No. 1, 91. Work was then directed to the production of the cytotoxin by culture of *Pasteurella haemolytica* and the conversion of culture supernatant into a vaccine. The impetus for development of such a vaccine partially resulted from the generation of anti-toxic immune response after natural exposure of animals to *P. haemolytica*. Calves vaccinated with leukotoxic culture supernate isolated from the culture of *P. haemolytica* produced both anti-toxic and bacterial agglutinating antibody. The so vaccinated calves were more resistant to experimental challenge than were counterparts vaccinated with bacterins or unvaccinated calves, as reported in "Immunity to *Pasteurella haemolytica* Cytotoxin", P. E. Shewen and B. N. Wilkie, 1982, Conf. Res. Workers Animal Disease, Chicago, Ill., Abstract 138.

As a result, production in vitro of the cytotoxin by *Pasteurella haemolytica* has become very much of interest in an attempt to make a suitable vaccine on a commercial basis for counteracting "Shipping Fever" pneumonia. To date, the only viable technique for the in vitro production of cytotoxin has required the addition of serum or blood to the culture medium and in particular the use of fetal calf serum. Any attempt to manufacture the cytotoxin in a serum-free medium by culturing *P. haemolytica* has resulted in what was thought to be an absence of produced cytotoxin because any assay for the cytotoxin was negative. Fetal calf serum is used as a seven percent solution which has been established to be the minimum amount needed to permit production of toxic culture supernate in RPMI 1640 medium. With the use of fetal calf serum or other stabilizing serum, heat-labile leukotoxin is made by culturing the *P. haemolytica* and harvesting the cytotoxic supernatant after approximately one hour of growth at 37° C. in the manner reported in the aforementioned article "Cytotoxin of *Pasteurella haemolytica* Acting on Bovine Leukocytes". The use of serum and particularly fetal calf serum in the manufacture of the cytotoxin complicates analysis of *P. haemolytica* antigens present in culture supernate, greatly increases the cost for vaccine production and introduces potentially harmful extraneous antigens into the vaccine preparations. Furthermore, the presence of the serum in the supernate maintains activity of the toxin, which is undesirable in the vaccine preparation.

SUMMARY OF THE INVENTION

According to an aspect of this invention, a serum-free medium containing the cytotoxin to leukocytes is prepared from a serum-free culture of *Pasteurella haemolytica*. The process comprises culturing *Pasteurella haemolytica* viable cells in a serum-free medium to produce the cytotoxin. A determinant of logarithmic phase growth of the viable cells is monitored. A liquid containing the cytotoxin is harvested from the medium upon detecting a predetermined characteristic of the determinant in the monitored logarithmic phase of cell growth. The predetermined characteristic corresponds to an optimum concentration of produced cytotoxin in the serum-free medium.

According to another aspect of the invention, the solution containing the cytotoxin may be converted into an animal vaccine.

According to another aspect of the invention, a vaccine effective against pneumonic pasteurellosis in cattle comprises a serum-free medium containing an inactive leukotoxin specific for ruminant leukocytes.

According to another aspect of the invention, a method for treating cattle to develop anti-leukotoxic immunity to pneumonic pasteurellosis comprises administering to cattle an effective protective amount of the serum-free vaccine.

BRIEF DESCRIPTION OF THE DRAWINGS

Preferred embodiments of the invention are shown in the drawings wherein:

FIG. 2 is a graph showing the relationship between the growth curve of *P. haemolytica* in serum-free medium and the optical density of the culture at 525 nm, where □----□ is growth curve, log₁₀ CFU per ml; and ┼────┼ is optical density at 525 nm.

DETAILED DESCRIPTION OF THE PREFERRED EMBODIMENTS

Figure 1:
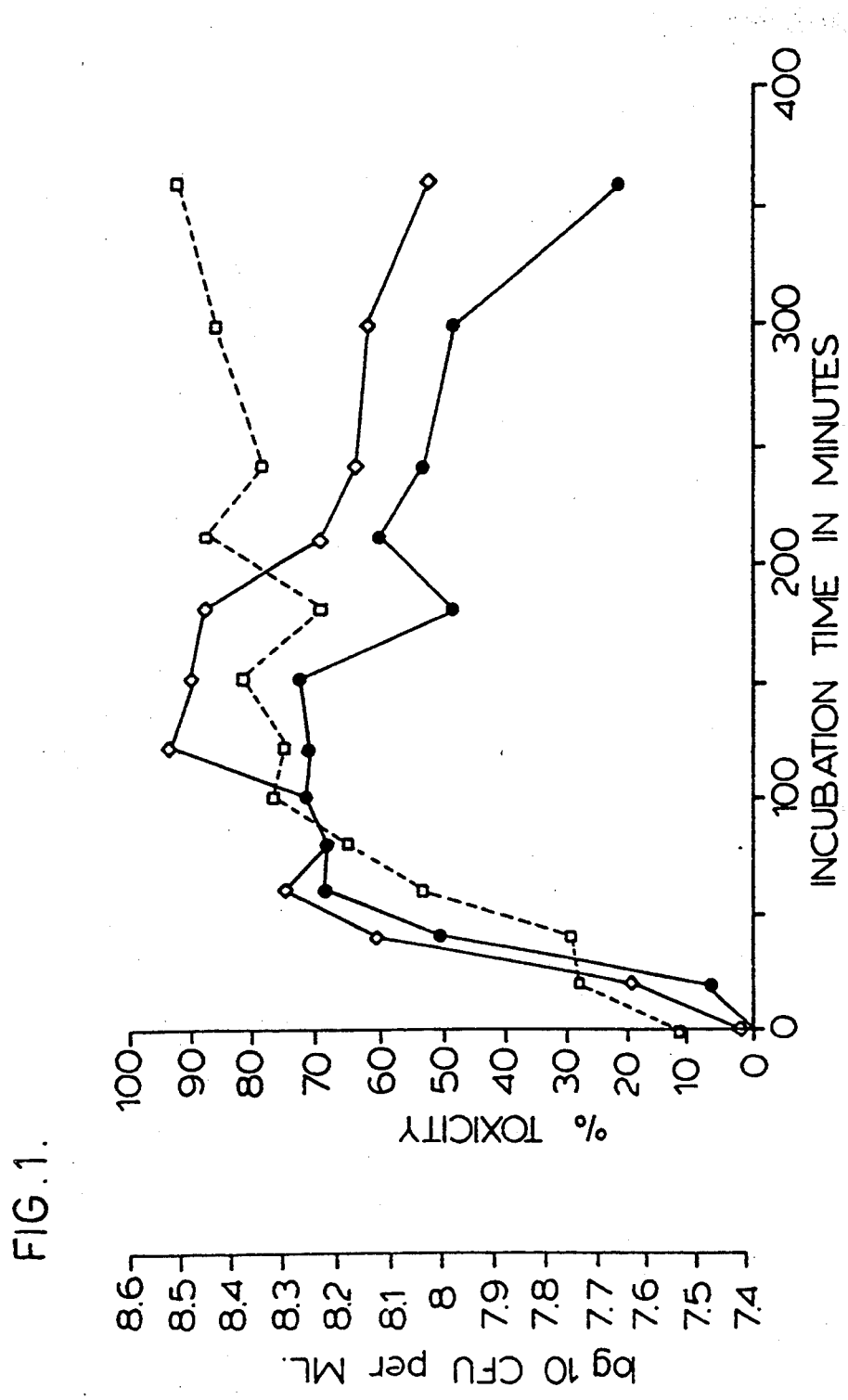
FIG. 1 is a graph showing the relationship of leukotoxic production to the growth curve of *P. haemolytica* in serum-free medium where □---□ is growth curve, $\log_{10}$ CFU per ml; ◇ — ◇ is total toxicity in culture supernate; and ●———● is heat-labile toxicity in culture supernate.

Although the mechanism is not fully understood as to the manner in which infection of cattle with *Pasteurella haemolytica* results in pneumonia and other infections such as mastitis in milking cows, it is realized that the preparation of vaccines based on *P. haemolytica* cells are inefficatious. Surprisingly, cattle vaccinated with vaccines based on bacterins have increased susceptability to the "Shipping Fever" pneumonia. In addition, immediate anaphylactoid reactions occur. Furthermore, the use of live bacteria as vaccines produce severe local reactions at injection sites and in common with live vaccines are problematic with respect to production, storage, distribution and use. However, a vaccine based on a cytotoxin prepared by culturing *P. haemolytica* has been shown to protect or prevent pneumonic pasteurellosis of cattle. It is thought that the cytotoxin, which is a leukotoxin specific for ruminant leukocytes, is an important virulence factor in the induction of pasteurella pneumonia. The use of fetal calf serum in existing processes for the production of cytotoxin and resultant conversion into vaccine was thought to be necessary because culturing *P. haemolytica* on a serum-free medium to produce cytotoxin did not result in the detectable presence of active cytotoxin in the culture supernate.

According to a preferred embodiment of this invention, *Pasteruella haemolytica* may be grown in a serum-free medium, such as RPMI 1640 medium which is available from GIBCO, Grand Island, N.Y. It has been discovered that the culture of *P. haemolytica* in a serum-free medium, such as RPMI 1640, produces the cytotoxin. However, it has been discovered that continued culture of *P. haemolytica* results in a disappearance of the cytotoxin either by loss of its toxicity or degradation thereof. It was discovered that the cytotoxin can be harvested from the culture medium of *P. haemolytica* in a serum-free medium at an appropriate time interval to optimize on the concentration of usable cytotoxin present in the medium. To determine the time period when to harvest the liquid containing the cytotoxin from the medium, the toxicity of the supernate of the culture medium was investigated over extended periods of culturing of the *P. haemolytica* to develop a relationship of leukotoxin production compared to the growth curve of *P. haemolytica* in the serum-free medium. With reference to FIG. 1, the growth curve for *P. haemolytica* is represented on the scale "Log₁₀ CFU per ml", where CFU represents colony-forming units. For extended incubation times in the range of 350 minutes, periodically supernatant was isolated and the toxicity of the cytotoxin in the supernate was analyzed. The total toxicity in culture supernate, along with the heat-labile activity of the cytotoxin in the culture supernate, were shown to rise rapidly with the logarithmic phase growth of the *P. haemolytica* cells and then commence falling off after incubation times greater than approximately 150 to 200 minutes insofar as the particular example shown in FIG. 1.

It becomes apparent from FIG. 1 that the optimum condition for harvesting the supernate is when cytotoxin is at its highest concentration, and as shown in FIG. 1, this is when the culture is in logarithmic growth phase. Therefore, in the culturing of *P. haemolytica* in the serum-free medium, a determinate of the logarithmic phase growth of viable cells has to be monitored to indicate when it is best to harvest the cytotoxin containing liquid. According to a preferred embodiment of this invention, the determinate of the logarithmic phase growth of the cells is the optical density of the culture medium.

With reference to FIG. 2, the relationship between the growth curve of the *P. haemolytica* similar to that of FIG. 1 is plotted with respect to optical density of the culture medium measured at a wavelength of 525 nm. On the basis of the results plotted in FIG. 1, an approximate tenfold increase in the colony forming units (CFU) per ml. indicates the time during which cytotoxin should be harvested from the medium. This corresponds with a change in optical density ranging from approximately 0.18 up to approximately 0.37 (FIG. 2). This corresponds with an incubation period of approximately 1.5 to 3 hours for the *P. haemolytica* in a serum-free medium such as RPMI 1640.

As illustrated in FIG. 1, bacterial growth commenced immediately upon inoculation of *P. haemolytica* into the serum-free medium RPMI 1640 without an appreciable lag phase. Detectable heat-labile toxic activity in culture supernate increased during early logarithmic growth, maintained a plateau in the late logarithmic stage and declined in stationary phase culture. From this growth curve, it was determined that the peak production of heat-labile toxin was achieved when bacteria had undergone a tenfold increase in CFU which corresponds with the already noted change in optical density. When the supernate is harvested at the optimum time, which has been established as the predetermined characteristic of optical density of approximately 0.37, it was also discovered that measurable toxicity of the harvested cytotoxin could not be evaluated unless fetal calf serum was added to the supernate to stabilize the toxicity of the cytotoxin. Therefore, in evaluating the toxicity of the cytotoxin, it was necessary to stabilize each supernate isolated from the culture at the times shown in FIG. 1 so that its toxicity could be evaluated. Alternatively, the culture supernate can be frozen immediately on isolation at −70° C. to retain toxicity without the addition of serum. The frozen supernate is retained at that temperature until analysis is conducted to determine the toxicity of the supernate at that particular time of isolation during the culture of *P. haemolytica*.

According to this invention, a process is provided for making the desired cytotoxin in a serum-free medium which provides a distinct advantage over the prior processes, wherein it was thought necessary to use fetal calf serum or other stabilizing serum in the medium to permit toxigenic growth of the bacteria in producing the desired cytotoxin. As is established with reference to the results in FIG. 1, it is only necessary to add serum to the supernate after isolation from the culture medium, i.e. at harvest, to stabilize and maintain the toxic activity of the desired cytotoxin. This is, of course, only necessary when it is desired to assay for the presence of cytotoxin in the supernate. Alternatively, the supernate can be frozen and maintained at −70° C. to retain toxicity of the cytotoxin. Otherwise, without the addition of serum, activity of the cytotoxin is rapidly lost in the supernate. This is desirable in the manufacture of vaccine, because it provides a non-toxic inactive cytotoxin in the vaccine medium which is not harmful to the recipient yet as discovered, the inactive toxin retains the ability to elicit an immune response in the animal.

The optimum time to harvest cultured supernate in isolating the cytotoxin for vaccine is during early to mid logarithmic growth of the *P. haemolytica*. It has been found that growth in the serum-free medium is sufficiently variable that a characteristic of a determinate of the growth of the bacterium must be monitored rather than specifying the specific time during growth of the bacterium at which harvest is to take place. A useful determinant, according to this preferred embodiment, is optical density where a change in optical density at 525 nm. from approximately 0.18 at commencement of culturing of a concentration of cells of approximately $10^7$ CFU per ml to 0.37 which corresponds to approximately $10^8$ CFU per ml. The corresponding duration of time needed for this tenfold increase in cell growth has been found to vary from 1.5 up to 3 hours for *P. haemolytica* A1.

After harvesting the supernate liquid containing the cytotoxin from the medium, a suitable vaccine may be prepared from the harvested liquid. A sample of the harvested liquid may be stabilized with fetal calf serum and assay conducted to determine and confirm toxicity of the produced cytotoxin. At harvest, the liquid is processed to remove extraneous matter. For example, the harvested liquid may be centrifuged and filtered to remove all solids which include cells, cell wall fragments, unwanted metabolites and the like, thereby providing a liquid which is cell free and which is relatively endotoxin free. Thus when the vaccine is administered, the likelihood of anaphylactoid reactions is minimized which is a problem with prior vaccines of this nature due to the presence of endotoxin in the cell wall of the gram negative bacterium *P. haemolytica*. It is appreciated that a variety of suitable techniques are available for isolating the cytotoxin and preparing the vaccine which are readily known to those skilled in the art. The selection of suitable techniques is primarily determined by the product to be prepared and the scale of commercialization.

The purified liquid is then treated in accordance with standard procedures in preparing a vaccine. The liquid is lyophilized to produce a stable composition when reconstituted in saline to the appropriate concentration for administration to animals. A preferred concentration is in the range of at least threefold. Various expedients may be added to the vaccine to improve its efficiency. Thus well known adjuvants may be added to the vaccine to optimize in the protection against pneumonic pasteurellosis in animals.

Preferred aspects of the invention are set out in the following Examples.

EXAMPLE 1

*Pasteurella haemolytica* Culture and Leukotoxin Production

Several colonies from an 18-hour blood agar plate of *P. haemolytica* type A1 were inoculated into 500 ml of brain-heart infusion broth in each of four 1 liter Erlenmyer flasks and grown for 4.5 hours at 37° C. on a rocking platform. The particular *P. haemolytica* serotype A1 used in this Example is on deposit at the American Type Culture Collection under accession no. ATCC 43720. During this period, the cultures were in the early logarithmic phase of growth. Bacteria were pelleted by centrifugation at 4,000×g for 10 minutes, pooled, and suspended to a concentration of approximately $10^7$ colony-forming units (CFU)/ml. This concentration was estimated spectrophotometrically. The cells were suspended in 1 liter of RPMI 1640 medium which is readily available from GIBCO, Grand Island, N.Y. The medium was placed in a 2 liter Erlenmeyer flask and incubated at 37° C. on a rocking platform. Before commencing of this incubation (time 0) and at specified time intervals thereafter, in the manner illustrated in FIG. 1, 6 ml samples were periodically removed aseptically from the culture and assayed as follows. The optical density was read at 525 nm. and the number of the CFU per milliliter was determined using a standard plate-count technique. After centrifugation at 6,000 ×g for 15 minutes, the supernate was filtered through a 0.22 um filter available from Millipore Corp., of Bedford, Mass. and a sample (0.5 ml) was checked for sterility by bacteriologic culture. The supernate was divided into two aliquots and 7% fetal calf serum (FSC) was added to one of these. One ml of each aliquot was heated at 56° C. for 30 minutes before evaluation for cytotoxicity. The production of heat-labile toxin was determined by subtracting heat-stable toxicity from total toxicity. When the optimum conditions for harvesting culture supernate had been determined, the stability of toxic activity was evaluated for various conditions of storage.

EXAMPLE 2

Cytotoxicity Assay

The toxic activity in culture supernate was determined by a microplate assay using as targets BL-3 cells, a bovine leukemia-derived B lymphocyte cell line obtained from G. Theilen, University of California, Davis, Calif. Alternatively, freshly harvested bovine alveolar macrophages or peripheral blood lymphocytes may be used; i.e., need ruminant leukocytes but the use of BL-3 cells is not obligatory. Cells were incubated in the presence of culture supernate for 1 hour at 37° C. Cell survival at the end of the assay was assessed by staining the remaining viable cells with the dye neutral red. Following solubilization of cells, dye uptake was determined as optical density (540 nm) using an automated spectrophotometer available from Titertek Multiscan, Flow Laboratories, Mississauga, Ontario. The percent toxicity for each test preparation was calculated as follows:

$$\% \text{ toxicity} = \frac{A - B}{A} \times 100$$

where

A=mean OD (optical density) of quadruplicate control wells, RPMI 1640 medium only;

B=mean OD (optical density) of quadruplicate wells containing the test preparation.

By way of this assay, the relationship of leukotoxin production to the growth curve of *P. haemolytica* can be evaluated in the manner illustrated in FIG. 1. When optimum conditions for harvesting the cytotoxin were determined, the harvested supernate was then evaluated for toxicity under various condition of treating the isolated supernate. Untreated supernate, supernate with 7% fetal calf serum added at harvest and supernate with 7% fetal calf serum added at test were evaluated to reveal that, from the standpoint of analyzing toxicity of the supernate, the best combination is the addition of 7% fetal calf serum added at harvest to the supernate, in order to maintain toxicity of the cytotoxin for assay. A second approach of freezing the supernate upon harvesting at −70° C. and maintaining it at −70° C. also retains the activity of the cytotoxin.

EXAMPLE 3
Evaluation of Immunogenicity of the Cytotoxin Vaccine

Having established the presence of the cytotoxin in the culture supernate, a vaccine is prepared therefrom. The filtered culture supernate is lyophilized and reconstituted to 5 mg/ml in sterile saline. A rapid technique to evaluate immunogenicity in animals is to conduct a study with mice wherein it is understood that with this type of cytotoxin, an immune reaction in mice confirms an immune reaction in other animals, including cattle. Balb/c mice each received by intraperitoneal injection 0.2 ml of the vaccine. The vaccine had no detectable toxic activity at the time of immunization. An additional five control mice received a similar injection of RPMI 1640 medium, similarly lyophilized and reconstituted. Mice were given four weekly immunizations. Sera from the mice were tested for ability to neutralize *P. haemolytica* leukotoxin 5 days after the last injection. Toxin neutralization was assessed using the neutral red assay after preincubation (1 hour, 37° C.) of cytotoxic culture supernate (toxin) prepared using 7% normal mouse serum with various dilutions of test sera. The results of the test are set out in following Table 1. The percent neutralization was calculated as:

$$\% \text{ neutralization} = \frac{C - D}{E - D} \times 100$$

where

C = mean OD (optical density) of quadruplicate wells containing toxin previously incubated with test mouse serum D = mean OD (optical density) of control wells containing toxin previously incubated with pooled normal mouse serum at the same dilution as C E = mean OD (optical density) of control wells containing RPMI 1640 plus normal mouse serum, at the same dilution as C.

The neutral red assay involved the evaluation of uptake of neutral red dye by unkilled cells which is, therefore, a measure of the immune response in the mice.

TABLE 1

Toxin Neutralizing Activity in Sera from Mice Immunized With Culture Supernate from *P. haemolytica* A1 Grown in Serum-Free Medium

| Immunization | | % Neutralization Serum Dilution | | | | Neutralizing Titer |
|---|---|---|---|---|---|---|
| Mouse | | 1/40 | 1/80 | 1/160 | 1/320 | (50% endpoint) |
| Culture: | 1 | 61 | 102 | 180 | 144 | >1/320 |
| Supernate | 2 | 98 | 106 | 114 | 76 | >1/320 |
| | 3 | 37 | 106 | 107 | 121 | >1/320 |
| | 4 | 90 | 97 | 145 | 99 | >1/320 |
| | 5 | 42 | 97 | 160 | 13 | 1/160 |
| Medium: | 1 | 0 | 5 | 0 | 0 | 0 |
| Alone | 2 | 0 | 12 | 7 | 4 | 0 |
| | 3 | 5 | 8 | 0 | 10 | 0 |
| | 4 | 0 | 0 | 0 | 0 | 0 |
| | 5 | 0 | 0 | 0 | 0 | 0 |

The leukotoxin produced in serum-free medium is immunogenic, inducing neutralizing activity in serum even when the material used for immunization is itself not demonstrably leukotoxic. This is a significant development insofar as the prevention of pneumonic pastereullosis. The vaccine can be prepared in a serum-free medium and, as a consequence, provide a serum-free vaccine containing leukotoxin which is inactive in its produced state yet is capable of eliciting immune response when administered to animals and in particular cattle. The vaccine is useful in the prevention of *P. haemolytica* pneumonia in ruminants. It is also potentially effective for treatment of other *P. haemolytica* infections such as mastitis. Since stability of the leukotoxin in the vaccine is not a problem, the vaccine has excellent storage properties and because of the absence of endotoxin, does not produce severe local reactions at injection sites or anaphylactoid reactions.

Although preferred embodiments of the invention have been described herein in detail, it will be understood by those skilled in the art that variations may be made thereto without departing from the spirit of the invention or the scope of the appended claims.

The embodiments of the invention in which an exclusive property or provilege is claimed are defined as follows:

1. A process for producing a non-toxic inactive cytotoxin specific for ruminant leukocytes comprising the steps of:
    (A) culturing an inoculum of *Pasteurella haemolytica* having an optical density of about 0.18 measured at a wavelength of 525 nm, in a serum-free medium for a period in the range of 1.5 to 3 hrs, so as to produce said cytotoxin;
    (B) periodically measuring the optical density of said serum-free medium;
    (C) upon detecting a value for the optical density of about 0.37, measured at a wavelength of 525 nm, which indicates the phase of logarithmic growth of the cells when an optimum concentration of cytotoxin is produced in said serum-free medium, separating supernatant liquid containing said cytotoxin from the resulting culture;
    (D) separating solids, including any of said cells, from the resulting supernatant liquid so as to obtain a *Pasteurella haemolytica* serum-free, cell-free solution of said cytotoxin which is essentially endotoxin-free.

2. The process of claim 1, additionally comprising step (E):
    adding serum to the resulting solution of step (D) so as to stabilize said cytotoxin for the purpose of analysis of toxic activity.

3. The process of claim 1, additionally comprising step (E):
    freezing the resulting solution.

4. The process of claim 1, wherein said separating in step (D) is carried by out by centrifugation or filtration.

5. The process of claim 1, wherein said *Pasteurella haemolytica* is *Pasteurella haemolytica* A1.

6. The process of claim 1, wherein said *Pasteurella haemolytica* serum-free, cell-free solution is admixed with a pharmaceutically acceptable serum-free carrier or diluent to obtain a serum-free vaccine effective against pneumonic pasteurellosis in cattle.

7. The process of claim 6, wherein said *Pasteurella haemolytica* serum-free, cell-free solution is lyophilized, and then reconstituted in sterile saline.

* * * * *